United States Patent
Neubiser

(10) Patent No.: US 11,104,876 B2
(45) Date of Patent: Aug. 31, 2021

(54) BIOREACTOR FOR BIOLOGICAL MATERIAL

(71) Applicant: Richard Neubiser, Antioch, IL (US)

(72) Inventor: Richard Neubiser, Antioch, IL (US)

(73) Assignee: TARGETED BIOSYSTEMS, LLC, Antioch, IL (US)

( * ) Notice: Subject to any disclaimer, the term of this patent is extended or adjusted under 35 U.S.C. 154(b) by 0 days.

(21) Appl. No.: 16/265,165

(22) Filed: Feb. 1, 2019

(65) Prior Publication Data

US 2019/0194592 A1    Jun. 27, 2019

Related U.S. Application Data

(63) Continuation-in-part of application No. PCT/US2018/027869, filed on Apr. 17, 2018.

(60) Provisional application No. 62/487,216, filed on Apr. 19, 2017.

(51) Int. Cl.
  *C12M 1/00*    (2006.01)
  *C12M 3/00*    (2006.01)
  *C12M 1/32*    (2006.01)

(52) U.S. Cl.
  CPC .......... *C12M 29/04* (2013.01); *C12M 23/12* (2013.01); *C12M 23/20* (2013.01); *C12M 23/38* (2013.01); *C12M 23/48* (2013.01); *C12M 29/20* (2013.01)

(58) Field of Classification Search
  CPC .............................. C12M 29/04; C12M 23/24
  USPC ...................................................... 435/297.1
  See application file for complete search history.

(56) References Cited

U.S. PATENT DOCUMENTS

| | | |
|---|---|---|
| 3,248,302 A | 4/1966 | Mackin |
| 4,839,292 A | 6/1989 | Cremonese |
| 4,886,690 A | 12/1989 | Davis et al. |
| 5,047,347 A | 9/1991 | Cline |
| 5,665,594 A | 9/1997 | Schwarz et al. |
| 5,693,537 A | 12/1997 | Wilson et al. |
| 5,707,869 A | 1/1998 | Wolf et al. |
| 5,714,384 A | 2/1998 | Wilson et al. |
| 5,858,770 A | 1/1999 | Perlman |
| 6,228,607 B1 | 5/2001 | Kersten et al. |
| 6,468,792 B1 | 10/2002 | Bader |
| 7,229,820 B2 | 6/2007 | Wilson |
| 8,158,426 B2 | 4/2012 | Wilson et al. |
| 8,158,427 B2 | 4/2012 | Wilson et al. |
| 8,168,432 B2 | 5/2012 | Wilson et al. |

(Continued)

FOREIGN PATENT DOCUMENTS

EP    3221442 A1 *  9/2017    ............ C12M 23/40

OTHER PUBLICATIONS

Sullivan et al., Assay Development in High Density MicroWell Plates: Use of Well Geometries, Format, Surface Modification and Optical Properties to Achieve Optimal Assay Performance, Apr. 1, 2001, JALA, vol. 6 Issue 2. (Year: 2001).*

(Continued)

*Primary Examiner* — Holly Kipouros
(74) *Attorney, Agent, or Firm* — The Roy Gross Law Firm, LLC; Roy Gross

(57) ABSTRACT

A method and system of and for handling, preserving, separating, filtering, collecting, manipulating, and/or culturing ex vivo biological material including red blood cells, white blood cells, and blood plasma within a bioreactor having a gas permeable membrane that allows for passive ventilation.

33 Claims, 10 Drawing Sheets

(56) References Cited

U.S. PATENT DOCUMENTS

| | | |
|---|---|---|
| 8,697,443 B2 | 4/2014 | Wilson et al. |
| 8,809,050 B2 | 8/2014 | Vera et al. |
| 9,410,114 B2 | 8/2016 | Wilson et al. |
| 9,441,192 B2 | 9/2016 | Wilson et al. |
| 2001/0024821 A1 | 9/2001 | Potter |
| 2003/0138433 A1 | 7/2003 | Newell et al. |
| 2004/0043481 A1 | 3/2004 | Wilson |
| 2004/0115798 A1* | 6/2004 | Ma .................. B01L 3/50853 435/288.4 |
| 2005/0266547 A1* | 12/2005 | Scherze .................. C12M 23/22 435/287.1 |
| 2007/0042490 A1* | 2/2007 | Welter .................. C12M 23/24 435/325 |
| 2007/0077181 A1* | 4/2007 | Youngbear ............. B01L 3/5085 422/400 |
| 2007/0254356 A1 | 11/2007 | Wilson et al. |
| 2008/0176318 A1 | 7/2008 | Wilson et al. |
| 2009/0305397 A1* | 12/2009 | Dodgson ............... B01L 3/5085 435/305.3 |
| 2010/0055774 A1 | 3/2010 | Wilson |
| 2010/0255576 A1 | 10/2010 | Wilson et al. |
| 2011/0117650 A1* | 5/2011 | Riordan ................ C12N 5/0667 435/378 |
| 2011/0312512 A1 | 12/2011 | Ammer et al. |
| 2012/0017505 A1* | 1/2012 | Bijl .......................... A01G 9/02 47/66.7 |
| 2014/0174329 A1 | 6/2014 | Nemitallah et al. |
| 2015/0293096 A1* | 10/2015 | Russell ............ G01N 33/56911 506/9 |
| 2016/0237392 A1* | 8/2016 | Lee .......................... C12M 41/40 |
| 2016/0250632 A1* | 9/2016 | Hong ...................... C12M 23/38 422/569 |
| 2018/0187137 A1* | 7/2018 | Dunbar ................. C12N 5/0656 |

OTHER PUBLICATIONS

Unterleuthner et al., An Optimized 3D Coculture Assay for Preclinical Testing of Pro- and Antiangiogenic Drugs, Jan. 31, 2017, SLAS (Year: 2017).*

English machine translation of document titled EP 3221442 provided by Espacenet (Year: 2016).*

Naor, Editorial: Interaction Between Hyaluronic Acid and Its Receptors (CD44, RHAMM) Regulates the Activity of Inflammation and Cancer, Feb. 8, 2016, Frontiers in Immunology, 7:39, pp. 1-4 (Year: 2016).*

"CELLine Bioreactor Flasks", <http://www.argos-tech.com/celline-bioreactors.html>, Retrieved on Apr. 30, 2019.

Kandlikar et al, "Biomedical Applications of Microchannel Flows", Heat Transfer and Fluid Flow in Minichannels and Microchannels, Oct. 24, 2013, 592 pages.

"A High-Throughput Static Culture Flask as an Alternative to Shake Flask Culture", IrvineScientific, pp. 1-6.

De Bartolo et al, "Long-term maintenance of human hepatocytes in oxygen-permeable membrane bioreactor", Biomaterials, Sep. 2006; 27(27): pp. 4794-4803, Epub Jun. 6, 2006.

"Multiuse Culture Flasks for Antibody and Protein Production", IrvineScientific, pp. 1-4.

International Search Report PCT/US2018/27869 Completed Jul. 11, 2018; dated Aug. 7, 2018 3 pages.

* cited by examiner

BIOREACTOR FOR BIOLOGICAL MATERIAL

CROSS REFERENCE TO RELATED APPLICATIONS

This application is a continuation of PCT/US2018/027869 filed on Apr. 17, 2018 entitled BIOREACTOR FOR BIOLOGICAL MATERIAL, which claims the benefit of U.S. Provisional Application No. 62/487,216 filed on Apr. 19, 2018. Both applications. Are incorporated herein by reference in their entirety.

FIELD OF THE INVENTION

The present invention relates to bioreactors for handling, preservation, separation, filtering, and collection of biological materials such as cells and tissues. Specifically, the present invention relates to systems and methods for handling, preserving, separating, filtering, collecting, manipulating, and/or culturing ex vivo hematological materials including red blood cells, white blood cells, and blood plasma within a bioreactor having a gas permeable membrane that allows for passive ventilation.

BACKGROUND OF THE INVENTION

Bioreactors are known and used to grow cells and tissues and can be used to grow cells used to treat patients, while also providing an environment for new research into cell creation and generation which may lead to life saving medical treatments.

Known bioreactors and cell growth systems include various devices and methods ranging from as simple Petri dishes to complex specimen flasks for use in extreme magnification microscopy. Bioreactor and cell growing media includes historic designs such as t-flasks, spinner flasks, gas permeable bags, and WAVE bioreactors that use diffusion to provide cell access to nutrients to provide maximum growth of cells. Other systems include complex and expensive systems that cost hundreds of thousands of dollars and include mechanical pumps and various other instrumentation to provide nutrients and remove cell waste from the systems.

Existing cell bioreactors, cell culture flasks, and cell growth systems include: U.S. Pat. No. 4,839,292 to Cemonese; U.S. Pat. No. 4,886,690 to Davis et al.; U.S. Pat. No. 5,047,347 to Cline; U.S. Pat. No. 5,665,594 to Schwarz et al.; U.S. Pat. No. 5,693,537 to Wilson et al.; U.S. Pat. No. 5,707,869 to Wolf et al.; U.S. Pat. No. 5,714,384 to Wilson et al.; U.S. Pat. No. 5,858,770 to Perlman; U.S. Pat. No. 6,228,607 to Kersten et al.; U.S. Pat. No. 6,468,792 to Bader; U.S. Pat. No. 7,229,820 to Wilson; U.S. Pat. No. 8,158,426 to Wilson et al.; U.S. Pat. No. 8,158,427 to Wilson et al.; U.S. Pat. No. 8,168,432 to Wilson et al.; U.S. Pat. No. 8,697,443 to Wilson et al.; U.S. Pat. No. 8,809,050 to Vera et al.; U.S. Pat. No. 9,410,114 to Wilson et al.; U.S. Pat. No. 9,441,192 to Wilson et al.; US20030138433 to Newell et al.; US20040043481 to Wilson; US20070254356 to Wilson et al.; US20080176318 to Wilson et al.; US20100055774 to Wilson; US20100255576 to Wilson et al.; and US20140174329 to Nemitallah et al.

Other existing systems include CELLine Bioreactor Flasks CL1000 (shown in http://www.argos-tech.com/cel-line-bioreactors.html); Heat Transfer and Fluid Flow in Minichannels and Microchannels—Kandlikar 2006; Irvine CELLine Bioreactor Flask (http://wheaton.com/media/catalogs/WBRO_035 Celline Irvine/files); Long-term maintenance of human hepatocytes in oxygen-permeable membrane bioreactor, Loredana De Bartolo, Biomaterials, May 10, 2006; and WHEATON CELLine Bioreactors Flask (http://wheaton.com/media/catalogs/WPDL_006B CELLine Bioreactors)

One major obstacle in designing bioreactors and cell growth systems involves providing a media for cells to receive adequate nutrients, while also disposing of cell waste. Some known systems try to address this problem by providing complex solutions and systems with many mechanical elements such as pumps, pressure chambers and various other instrumentality. However, these systems are prohibitively expensive and are not effective for use in a general sense and for a laboratory or medical office.

Furthermore, existing bioreactors do not provide a cost effective and ubiquitous solution to provide a system for capturing and incubating cells, cell tissue, and other biological material.

The present invention is directed towards providing a solution over the prior art that allows for a solving these problems.

SUMMARY OF THE INVENTION

To improve upon the prior art, an object of the present invention is to provide a method and system of and for capturing and incubating cells and cell tissue.

An object of the present invention is to provide a single closed bioreactor system for capturing and incubating cells, cells tissues, or other biological material including a gas permeable membrane that allows for passive ventilation of system while maintaining the interior sterility of the system.

Another object of the present invention is to provide a bioreactor having a gas permeable membrane on top that allows for passive ventilation for the cells within the bioreactor.

Another object of the present invention is to provide a closed system that allows for gas transpiration, such that $CO_2$ is released out and $O_2$ passes into the device.

Another object of the invention is to allow for cell waste to pass through and out of the system without using a mechanical pump.

Another object of the present invention is to provide a system for cell growth, wherein the system provides and maintains interior sterility during use.

Another object of the present invention is to provide a system including at least one input and/or output port or receptacle for the introduction or extraction of biological or other material while maintaining interior system sterility.

Another object of the present invention is to provide a system including a selectively permeable material allowing for cell incubation via passive gas transpiration thus facilitating multi-day or week-long manipulation of the cells in a starting culture container without the use or need of pumps or mechanically induced motion.

Another object of the present invention is to provide a system that allows for cell growth in a small setting, such for allowing a small laboratory or medical office to grow cells and run tests based upon the cells grown in the bioreactor.

Another object of the present invention is to provide a system including a selectively permeable material allowing for cell incubation via passive gas transpiration wherein an interior surface of the culture system is at least partially hydrophilic whereby any introduced antigen adheres to at least a portion of the culture system interior.

Another object of the present invention is to provide a system, the system including a selectively permeable material allowing for cell incubation via passive gas transpiration wherein an interior surface of the culture system includes a microstructure.

Another object of the present invention is to provide a system, the system including a gas permeable membrane comprising a Class V1 polydimethylsiloxane or similar gas permeable silicon, fluoro-ethylene-propylene, or other natural or synthetic gas permeable exchange membrane.

Another object of the present invention is to provide a closed system that allows for coating an antigen on the bottom surface of the closed system that will then facilitate selection of subsets of various types of blood cells, usually positively, (but could be negative selection as well), whereby a specific antibody on the cell surface identifies the specific antigen and the cell attaches and is caught in the device.

Another object of the present invention is to provide a closed system with ability to capture specific cells coming from a specific patient, and also allows for the expansion/maturation (via growth factors and cell culture media sterilely introduced via PVC tubing) of those cells for re-infusion to that patient.

Another object of the present invention is to provide a system with a gas permeable membrane at the top to allow the cells to transpire in an incubator for a period of days.

Another object of the present invention is to provide a system that takes certain blood cells ex vivo and grows them in a bioreactor and then reintroduces the grown cells back into the human body to "jump start" the immune system.

Another object of the present invention is to provide an efficient and cost-effective system that allows for optimal nutrition to reach cells, while disposing of cell waste by using passive ventilation within the system.

These and other objects of the invention are achieved by providing a closed system of and for collecting and incubating living cells or other biological material comprising a housing configured to house living cells or other biological material; and a gas permeable membrane, wherein the housing allows for multi-day to multi-month incubation and manipulation of the living cells or other biological material within the interior of the housing without the use of pumps or mechanically induced motion.

In certain embodiments, the gas permeable membrane is medical grade.

In certain embodiments, the gas permeable membrane provides passive gas exchange of and for the cells or other biological material.

In certain embodiments, the gas permeable membrane is located on an exterior surface of the housing.

In certain embodiments, the system further includes a frame support configured to hold the gas permeable membrane on the exterior surface of the housing.

In certain embodiments, the gas permeable membrane fully surrounds the frame support, so as to encompass the exterior surface of the frame support.

In certain embodiments, the frame support is porous.

In certain embodiments, the system prevents ballooning of the gas permeable membrane if pressure is induced by liquid or air to facilitate emptying of the housing for the purpose of washing the living cells or for the purpose emptying the housing for living cells final recovery.

In certain embodiments, the frame support is attached to the housing by at least one of the group consisting of friction or interference fit, friction or interference fit with a sealing agent, a screw, a gasket, sonic welding, laser welding, and combinations thereof.

In certain embodiments, the housing includes a sidewall, wherein the sidewall includes a lip, wherein the frame support fits within the lip to secure the frame support to the housing.

In certain embodiments, the gas permeable membrane is configured to extend beyond the lip in the sidewall of the housing, the gas permeable membrane configured to seal the system such that all gases entering or existing the system must pass through the gas permeable membrane.

In certain embodiments, the housing includes a flange, the flange configured to allow a user to hold the system.

In certain embodiments, the housing includes supports. In certain embodiments, the supports are feet.

In certain embodiments, the supports are configured so that the housing is stackable on a second housing.

In certain embodiments, the housing is rectangular, square, or circular.

In certain embodiments, the housing is made from injection molded polystyrene or other acceptable materials.

In certain embodiments, certain configurations of the system are designed and intended to be inserted into a centrifuge.

In certain embodiments, the system is a closed system which allows gas exchange such that carbon dioxide is exchanged into or out of the system and oxygen passes into or out of the system.

In certain embodiments, the system allows for other desired or undesired gases to be exchanged.

In certain embodiments, the system is a closed system which allows for selected gases to pass in and out of the system.

In certain embodiments, the gas pressure within the system is greater than atmospheric pressure.

In certain embodiments, the housing further includes gas adjusted culture media located within the interior of the housing, the gas adjusted culture media configured to support the living cells or other biological material.

In certain embodiments, the culture media may over fill or under fill the housing within the system.

In certain embodiments, the interior of the housing is sterile and maintains sterility during system by use of at least one medical grade sterile connection or functionally closed sterile docking port.

In certain embodiments, the system includes at least one input and/or output port or receptacle for the introduction or extraction of living cells, other biological material, and/or media, cytokines, growth factors, antibodies, chemicals, or tissue fragments.

In certain embodiments, the system includes at least one input and/or output port configured with pre-attached sterile and dockable tubing to maintain sterility of the system.

In certain embodiments, an interior surface of the housing is at least partially hydrophilic, and wherein an agent introduced to the interior of the housing adheres to at least a portion of the housing interior surface.

In certain embodiments, the agent is selected from the group including an antigen, an antibody, a major histocompatibility immune complex (MHC), a retronectin reagent, and combinations thereof.

In certain embodiments, the agent adheres to the housing via a charge related to the internal surface of the housing.

In certain embodiments, the interior surface of the housing includes a microstructure.

In certain embodiments, the microstructure is selected from the group including a coating solution, a gel coating solution, a retronectin reagent, a cytomatrix, microbeads, larger or macro polystyrene beads, and combinations thereof.

In certain embodiments, the beads are 2 mm sized polystyrene beads. In certain embodiments, the beads are a "cytomatrix", i.e. three-dimensional matrices for cells to grow inside or even within a gel.

In certain embodiments, the gas permeable membrane is selected from the group including a non-Class V1 polydimethylsiloxane, a medical grade Class V1 polydimethylsiloxane or a similar gas permeable silicon, a fluoro-ethylene-propylene, a natural gas permeable exchange membrane, and combinations thereof.

In certain embodiments, the housing includes an antigen adhering capability to a gravitational bottom surface of the interior of the housing for selectively collecting subsets of various types of blood cells, wherein a specific blood cell antibody identifies the specific antigen for selectively collecting subsets of various types of cells within the interior of the housing.

In certain embodiments, the gas permeable membrane is located at or near the top of the housing to facilitate cell incubation for a period of days to weeks via selective gas exchange.

In certain embodiments, the gas permeable membrane is located at or near the top of the housing to facilitate cell incubation for a period of weeks to months via selective gas exchange.

In certain embodiments, the gas permeable membrane is located on or about a side wall of the housing to provide for increase release of cell waste products.

Other objects of the invention are achieved by providing a system and method of and for collecting and incubating living cells or other biological material, wherein the housing is configured to provide for the growth, expansion, and/or maturation of specific cells coming from a patient via a growth factor and/or a cell culture media, wherein specific cells are sterilely introduced into the system, and the selected cells grown, expanded, and/or matured and then taken from the system and reinfused to the patient and/or cryopreserved.

In certain embodiments, the housing is configured to provide for the growth, expansion, and/or maturation of specific cells coming from a patient via a growth factor and/or a cell culture media, wherein the specific cells are sterilely introduced into the system, and the selected cells grown, expanded, and/or matured and then taken from the system and infused to a donee and/or cryopreserved.

In certain embodiments, the system receives an ex-vivo collection of a patient's living cells, wherein the introduction to and incubation of the collected living cells within the interior of the housing, and the reintroduction of the incubated living cells back to the patient to stimulate, activate, support, enhance, change, down regulate, up regulate, or other manipulations whereby making it possible to recognize and kill cancer cells, regulate or kill autoimmune cells, and other manipulations of the immune system to create a normally functioning immune system.

In certain embodiments, the system facilitates the ex-vivo manipulation of a donor's cells, the introduction to and incubation of the collected cells within the interior of the housing, and the introduction of the incubated cells to a donee to stimulate, activate, support, enhance, change, deregulate, up regulate, or other manipulation whereby making it possible to recognize and kill cancer cells, regulate or kill autoimmune cells and other manipulations of the immune system to create a normally functioning immune system.

In certain embodiments, the system is configured for cell introduction, selection, maturation, and expansion within the system for incubation of the desired cells within the interior of the housing, and the reintroduction of the incubated cells back to the patient for the improvement and/or the enrichment of their immune system.

Other objectives of the invention are achieved by providing a method of and for collecting and incubating living cells or other biological material the method comprising the steps of: providing a system including a housing configured to house cells or other biological material; providing a gas permeable membrane; and incubating the cells or other biological material within the system without the need for pumps or mechanically induced motion; wherein the system provides for multi-day to multi-month incubation and manipulation of the cells or other biological material within the interior of the housing.

In certain embodiments, the gas permeable membrane allows for passive ventilation of the housing to provide passive gas exchange of and for the cells or other biological material.

In certain embodiments, the gas permeable membrane is medical grade.

In certain embodiments, the system is closed and allows for gas exchange such that carbon dioxide is released out of and into and oxygen passes out of and into the system.

In certain embodiments, the housing interior is sterile and maintains sterility during system use.

In certain embodiments, an interior surface of the housing is at least partially hydrophilic.

In certain embodiments, the method includes introducing an antigen to the housing interior to adhere to at least a portion of the housing interior surface.

In certain embodiments, the method includes comprising providing an antigen adherence capability from the charge characteristics of the gravitational bottom surface of the housing interior for selectively collecting subsets of various types of blood cells, whereby a specific blood cell antibody identifies the specific antigen for selectively collecting subsets of various types of cells within the housing interior.

In certain embodiments, the method includes a configuration for differentiating between an antigen positive and antigen negative reaction of cells, whereby a specific blood cell antibody identifies the specific antigen for selectively collecting subsets of various types of cells within the interior of the housing.

In certain embodiments, unwanted cells are adhered within the device and wanted cells are transferred to a separate collection container.

In certain embodiments, the method captures specific living cells coming from a patient, and provides for the growth, expansion, and/or maturation of the living cells via a providing growth factor and/or a cell culture media being introduced into the system, and then capturing and removing the grown, expanded, and/or matured living cells from the system and reinfusing the cells to the patient.

In certain embodiments, the method captures specific living cells coming from a donor, and provides for the growth, expansion, and/or maturation of the living cells via providing a growth factor and/or a cell culture media being introduced into the system, capturing and subsequently releasing the adhered and suspended living cells via shaking the device or using a compatible approved agent for removing the grown, expanded, and/or matured living cells from the system, and infusing the living cells to a donee.

In certain embodiments, the compatible approved agent is Trypsin.

In certain embodiments, the method includes collecting ex-vivo a patient's cells, introducing to and incubating the collected living cells within the housing interior, and reintroducing the incubated cells back to the patient to stimulate, activate, support, enhance, change, down regulate, up regulate, or other manipulations whereby making it possible to recognize and kill cancer cells, regulate or kill autoimmune cells and other manipulations of the immune system to create a normally functioning immune system.

In certain embodiments, the method includes collecting ex-vivo of a donor's living cells, introducing to and incubating the collected living cells within the housing interior, and introducing the incubated cells to a donee to stimulate, activate, support, enhance, change, down regulate, up regulate, or other manipulation whereby making it possible to recognize and kill cancer cells, regulate or kill autoimmune cells and other manipulations of the immune system to create a normally functioning immune system.

In certain embodiments, the method includes locating the gas permeable membrane at the gravitational top of the housing to facilitate cell or other biological transpiration and/or incubation for a period of days to weeks.

In certain embodiments, the method includes locating the gas permeable membrane at the gravitational top of the housing to facilitate cell or other biological transpiration and/or incubation for a period of months to years.

Other objects of the invention and its particular features and advantages will become more apparent from consideration of the following drawings and accompanying detailed description. It should be understood that the detailed description and specific examples, while indicating the preferred embodiment of the invention, are intended for purposes of illustration only and are not intended to limit the scope of the invention.

DETAILED DESCRIPTION OF THE INVENTION

In the following description, numerous details are set forth for the purpose of explanation. However, one of ordinary skill in the art will realize that the invention may be practiced without the use of these specific details. For instance, the techniques described below are described in a specified order, but other embodiments may change the order of the operations while still embodying the current invention.

In certain embodiments, the inventive method and system comprises a base or housing defining a container or cavity.

In certain embodiments, the inventive method and system comprises a structure with adherence properties.

In certain embodiments, the inventive method and system comprises a housing with a selective gas permeable material.

In certain embodiments, the inventive method and system comprises at least one fluid communicating port.

In certain embodiments, the inventive method and system is capable of and for capturing and incubating singular or multiple blood cells dependent upon blood cluster designations or blood cluster markers using a selected antigen or a plurality of selected antigens, the system including a selectively permeable material allowing for blood cell incubation via passive gas transpiration thus facilitating multi-day or multi-week long manipulation of the cells in a starting culture housing or container without the use or need of pumps or mechanically induced motion.

Figure 1:
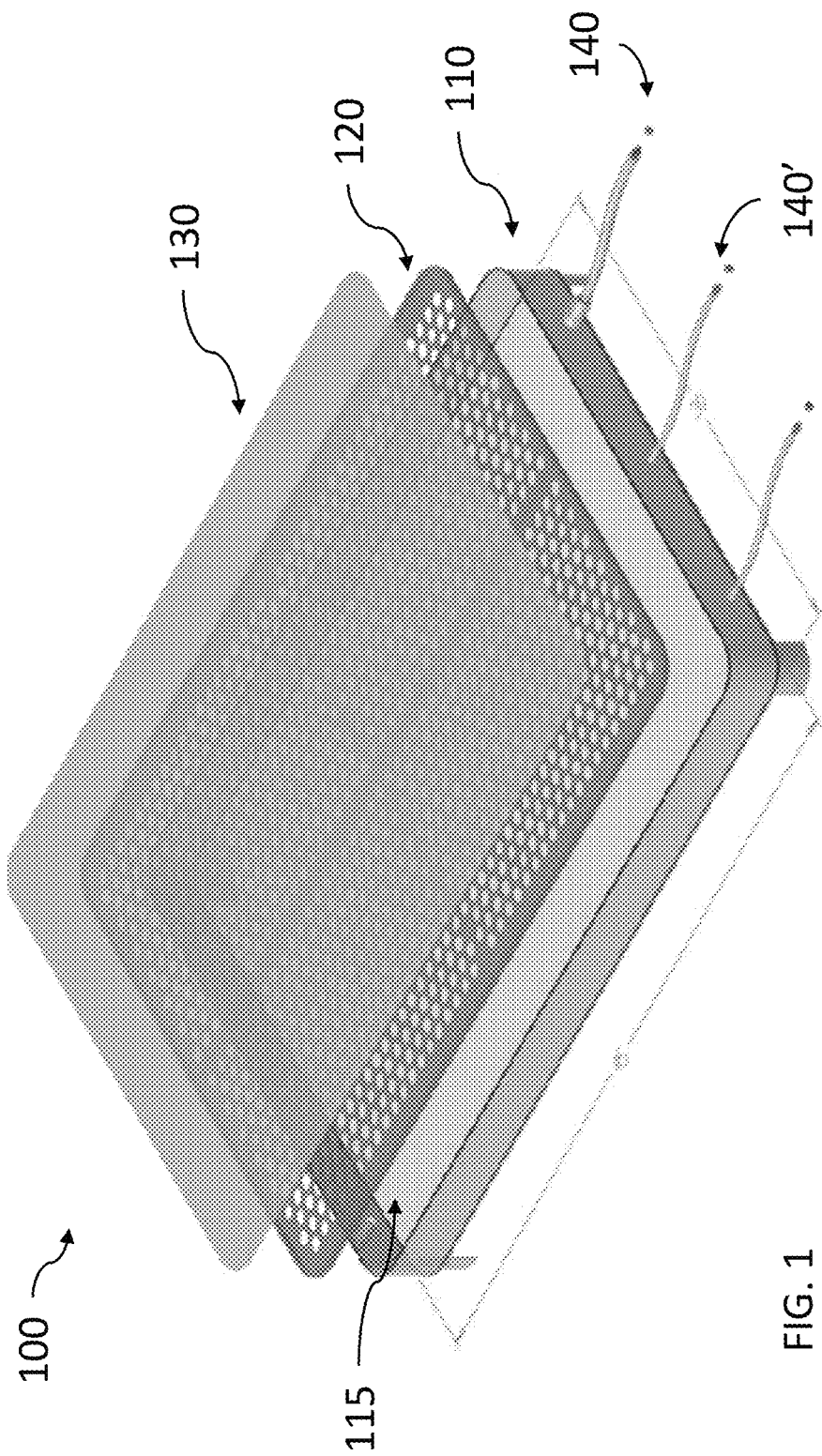
FIG. 1 is a diagram of an embodiment of the present invention in a flat or horizontal configuration and position.

As shown in FIG. 1, an exemplary embodiment of a present inventive capture and incubation housing or container (100) is depicted.

A culture base (110) is provided which at least in part defines a cavity, troth, or reservoir (115) for containing or holding a culture nutrient solution and/or other materials required for the capture and/or incubation of singular or multiple cells and cell types.

In certain embodiments of the inventive capture and incubation housing or container (100) includes a microstructure (120) which may be suspended within the cavity, troth, or reservoir (115) for and on which cells, antigens, or other biological materials or chemicals may adhere. It is also contemplated in certain embodiments that the microstructure (120) may be a three-dimensional matrix or other type scaffolding onto which cells, antigens, or other biological materials or chemicals may adhere.

In certain embodiments, it is contemplated that the culture base (110) and/or microstructure (120) may be manufactured via injection molding or by other means of shaping a Class V1 styrene or similar plastic, and be capable of sterilization via commonly known methods such as but not limited to; gas or liquid ethylene oxide, chlorine dioxide, hydrogen peroxide, gamma ray, or electron beam sterilization.

If the culture base (110) and/or microstructure (120) comprise material which is non-adherent to cells or other biological material (i.e. hydro and/or lipid phobic); if desired, gamma ray or electron beam sterilization methods may preferably be used to render the culture base (110) and/or microstructure (120) adherent (i.e. hydrophilic and/or lipophilic).

In certain embodiments of the present invention, the capture and incubation housing or container (100) includes a selective gas permeable material (130).

In certain embodiments of the present invention, the capture and incubation housing or container (100) comprises a selective gas permeable material (130) preferably capable of allowing desired oxygen and carbon dioxide transfer and/or exchange.

In certain embodiments of the present invention, the capture and incubation housing or container (100) comprise a selective gas permeable material (130) preferably capable of allowing desired oxygen and carbon dioxide transfer while maintaining interior system sterility.

Figure 2:
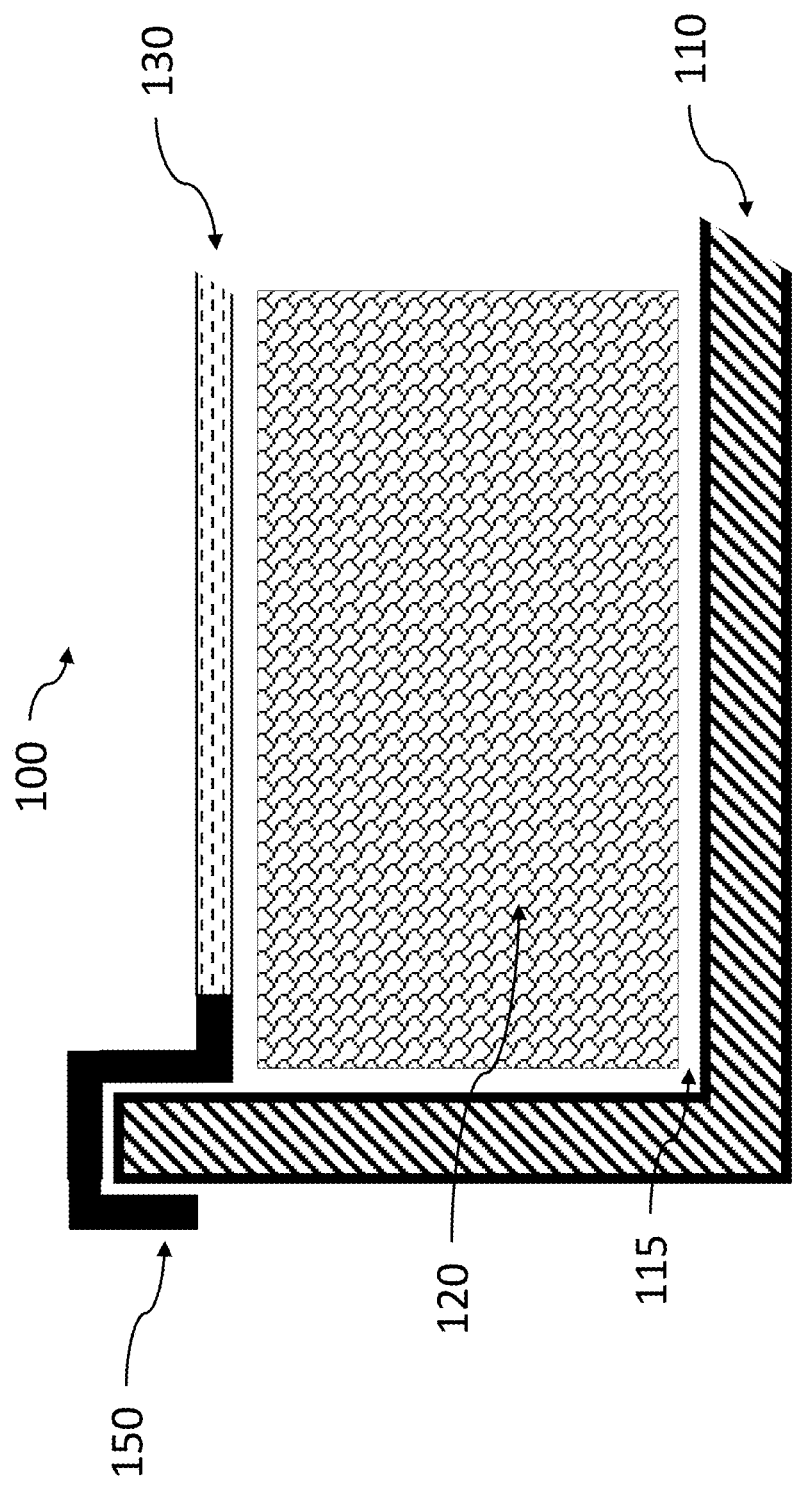
FIG. 2 is a diagram of an embodiment of the present invention depicting the seal of a top plate or lid to a culture base upper edge.

In certain embodiments of the present invention, the capture and incubation housing or container (100) includes a lid or frame (FIG. 2, 150) to support, secure, and/or affix the selective gas permeable material (130) above or abutted against the cavity, troth, or reservoir (115).

In certain embodiments of the present invention, the capture and incubation housing or container (100) culture base (110) includes at least one input and/or output port or receptacle (140) for the introduction or extraction of biological or other material to and from the cavity, troth, or reservoir (115) of the culture base (110).

In certain embodiments of the present invention, the culture base (110) includes at least one input and/or output port or receptacle (140) for the introduction or extraction of biological or other material to and from the cavity, troth, or reservoir (115) while maintaining interior system sterility.

In an embodiment of the present invention, the culture base (110) includes at least one heat source (Not Shown) to establish and maintain a desired interior incubation temperature of the cavity, troth, or reservoir (115).

One dynamic theory of operation of the present embodiment of the cell capture and incubation housing or container (100) may be as follows:

A capture and incubation housing or container (100) including a culture base (110) defining a cavity, troth, or reservoir (115) a microstructure structure (120) may be "pre-loaded" with a suitable nutrient media and desired adhered capture antigen to "snag" or "hook" a desired biological material such as by way of example and not limitation, white blood cells, dependent upon the cell's cluster designation or cluster marker. When a patient's whole blood is introduced to the cavity, troth, or reservoir (115) of the capture and incubation housing or container (100) via the at least one input and/or output port or receptacle (140), adhered antigens "capture" desired white blood cells. Once a desired quantity of white blood cells is captured, remaining whole blood components may then be removed and replaced with a desirable nutrient media for incubating and/or growing the captured white blood cells over a period of hours to days or weeks. After captured cell incubation, growth, treatment, and/or manipulation; further biological material or chemicals may be introduced to the capture and incubation housing or container (100) to "release" the adhered cells and/or antigens for immediate or eventual reintroduction to the patient or a donee.

In one embodiment of the present invention, via an additional input and/or output port or receptacle (140') a patient's whole blood may be purposefully and continuously recirculated through the capture and incubation housing or container (100) if desired.

In one embodiment of the present invention, the capture and incubation housing or container (100) may be used to capture and/or incubate bacterium, viruses, prions, spores, fungi, and the like.

In certain embodiments of the invention, a lid or frame (150) supporting securing and/or affixing the selective gas permeable material (130) above or abutted against the cavity, troth, or reservoir system has a series of holes such that $CO_2$ is released out and $O_2$ passes into the system.

In certain embodiments of the invention, a layer of gas permeable plastic sheeting is affixed to a ventilation scaffold to create a simple, yet effective bioreactor. Furthermore, the system includes tubing at the edges of the bioreactor functional to provide ingress and egress of pre-selected blood cells coming from the use of an apheresis machine, or other devices presently available to the practitioner or researcher. In certain embodiments, the system works with using whole blood cells and cells derived from buffy coats, adipose (fat from the abdomen) derived tissue, cells for MSC selection.

In certain embodiments of the invention, the system allows for not only the capture of specific cells, but also offers passive gas exchange of the housing or container to allow a multi-day or multi-week manipulation of cells in the starting container without use of mechanical pumps or mechanical motions.

In certain embodiments of the invention, the interior of the system housing or container (100) interior is coated with a desired antigen for the purpose of "snagging" or to "snag" a certain cell type.

In certain embodiments of the invention, the system housing or container (100) interior is coated with styrene plastic. In and of itself styrene plastic is hydrophobic, that is nothing aqueous will adhere to its surface. However, by use of gamma irradiation the styrene plastic surface can be made hydrophilic in order to render the housing or container interior adherent to cells, antigens, and the like. Once accomplished, injection via a port and pre-attached tubing of an antigen in liquid form that is specific to a particular TARGET BLOOD CELL whereby it is incubated and or manipulated as desired.

In certain embodiments of the invention, the system allows for the sterile ingress or egress of fluids or gases via known and FDA approved sterile connection and/or docking techniques.

In certain embodiments of the invention, the gas permeable membrane (130) comprises Class V1 PDMS or similar gas permeable (preferably and predominately $O_2$ and $CO_2$ permeable) silicon, FEP, or other natural gas permeable exchange membranes.

In certain embodiments of the invention, the system is used to capture a single or multiple blood cells with an antigen to a chosen capability defined by that cells CD marker. The marker could be CD4, CD8, CD14, CD19, and/or CD34 and so on. This is accomplished by conjugation of an antigen to an antibody surface marker on a particular chosen blood cell for ex vivo manipulation. Blood cells have surface markers that have designated antibodies. Science has the ability to manufacture antigens (the bacteria or virus or other") that certain blood cells are on the constant look out for to prevent or ultimately cure an ailment; think of those ailment fighting cells as having hooks that can only "snag" one particular antigen. At the time that an immune fighting cell detects a foreign bacteria or virus a cascade of events happens. In some people or with certain diseases there is a breakdown of the immune signaling and the disease progresses into problems such as cancer.

Figure 3:
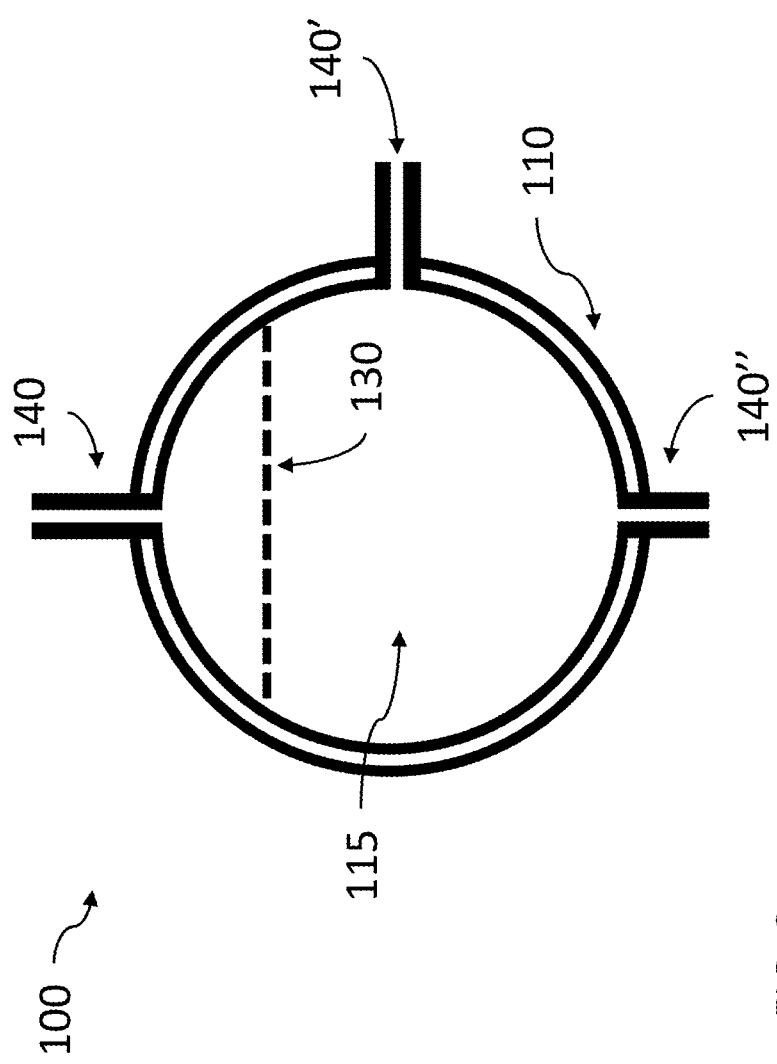
FIG. 3 is a diagram of an embodiment of the present invention in a round or spherical configuration culture base.
Figure 4A:
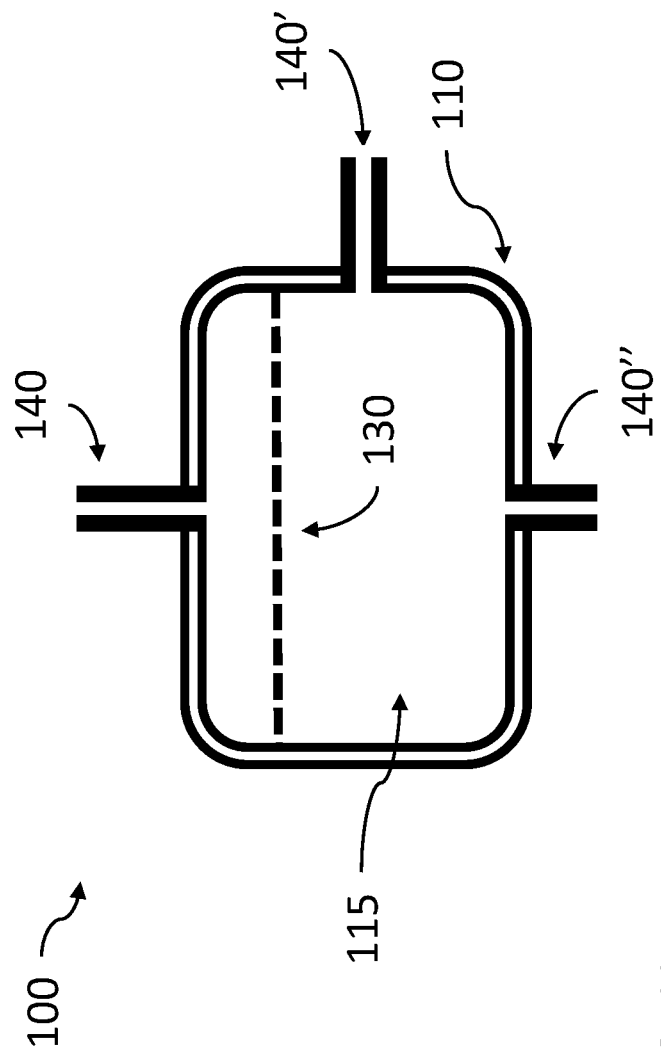
FIG. 4A is a diagram of an embodiment of the present invention in a modified spherical or rounded rectangular configuration culture base.

As depicted in FIGS. 3 and 4A, the system capture and incubation housing or container (100) culture base (110) may be of a round, spherical, modified spherical, or rounded rectangular, other shape to provide additional volume or culture depth to the system. The system capture and incubation housing or container (100) is shown having a selective gas permeable material (130) as well as ports into the system.

Figure 4B:
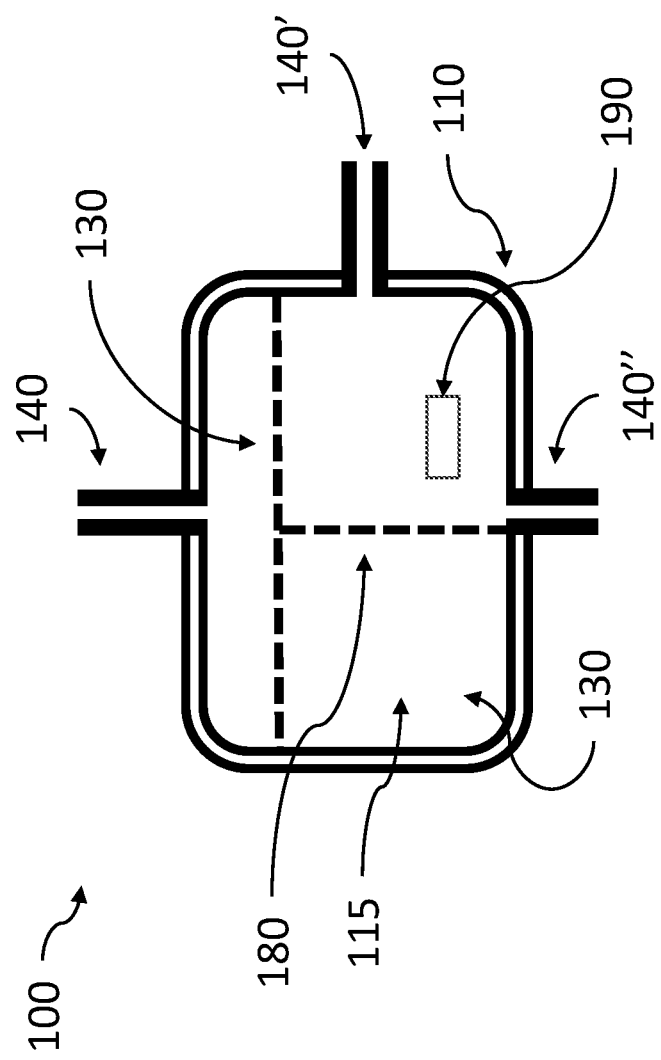
FIG. 4B is a diagram of an embodiment of the present invention in a modified spherical or rounded rectangular configuration culture base.

As shown in FIG. 4B, filter or vertical separation member (180) is shown as well as bar, which is magnetic (190). Magnetic bar (190) is used for scraping the bottom of the container (100) to encourage cell release for cells stuck to the bottom adherent complex. This would aid in drawing a small portion of the cells to an exit port or scrape the entire bottom for total cell release. The bar (190) may be coated with Teflon® or silicon or other inert material.

Figure 4C:
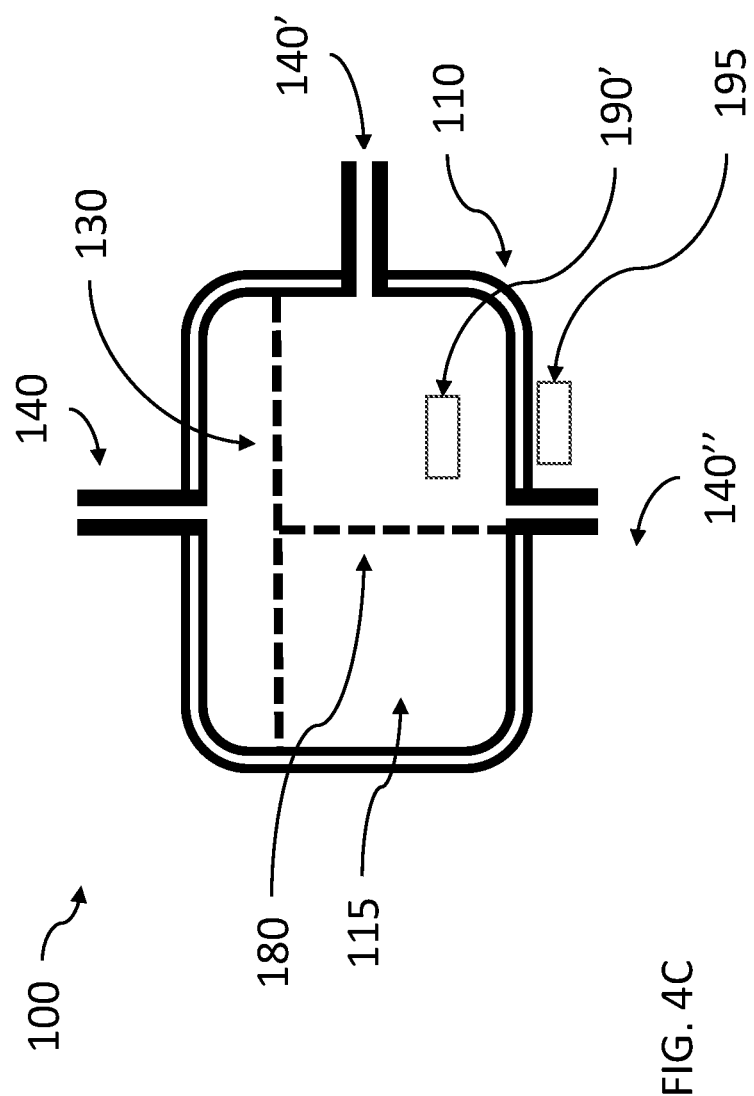
FIG. 4C is a diagram of an embodiment of the present invention in a modified spherical or rounded rectangular configuration culture base.
Figure 5A:
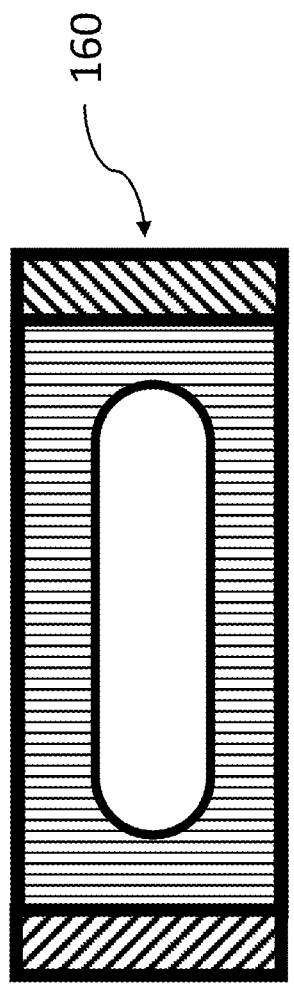
FIG. 5A is a diagram of an embodiment of the present invention depicting a culture base support or pedestal.
Figure 5B:
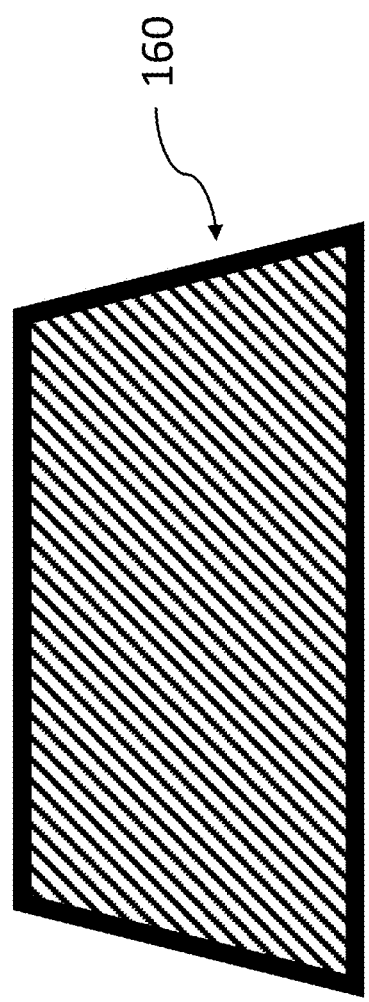
FIG. 5B is a diagram of an embodiment of the present invention depicting a culture base support or pedestal.
Figure 6:
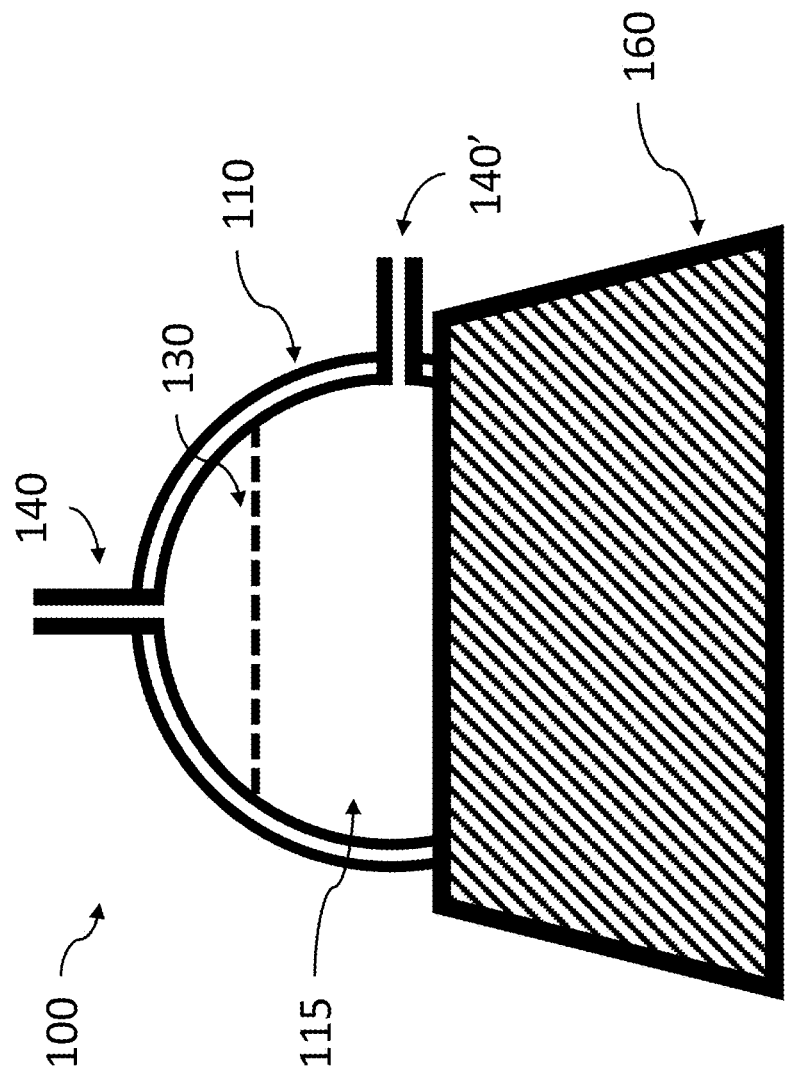
FIG. 6 is a diagram of an embodiment of the present invention depicting a round or spherical configuration culture base resting in a culture base support or pedestal.
Figure 7:
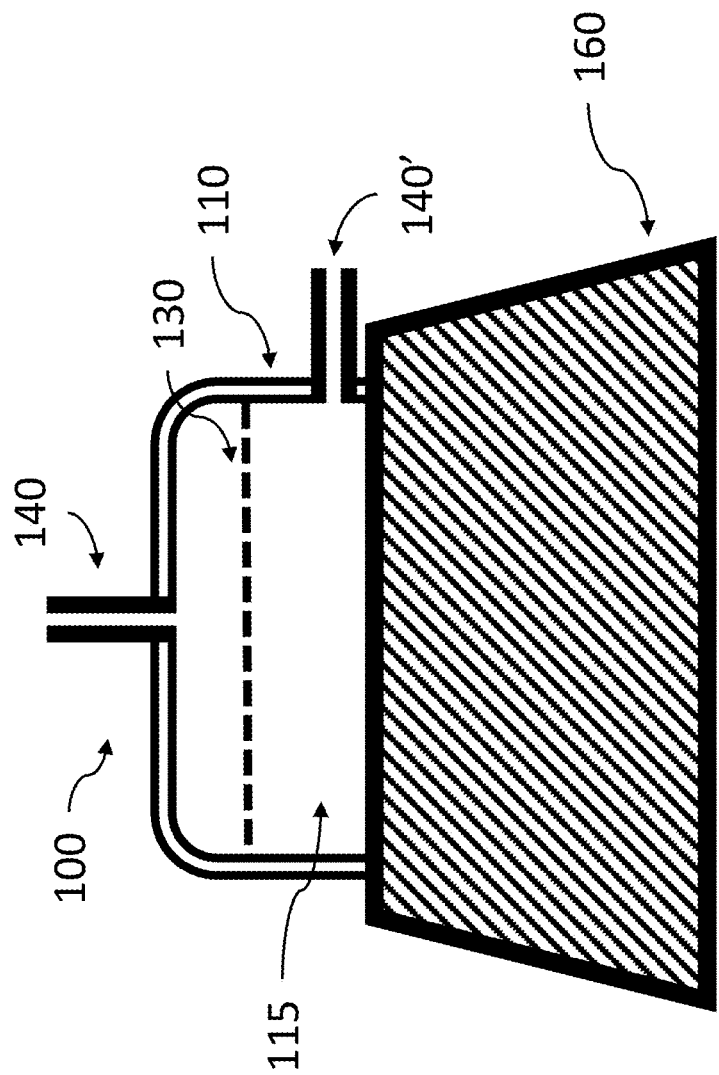
FIG. 7 is a diagram of an embodiment of the present invention depicting a modified spherical or rounded rectangular culture base resting in a culture base support or pedestal.

As shown in FIG. 4C, metallic bar scrapper (190') inside the device is not a magnet, but rather it would be metallic and would be controlled by an external magnet (195). One could position the metallic bar scrapper (190') by flipping the device over, guide the metallic bar scrapper (190') over a specific area attracted through the membrane, and then from the bottom using the external magnet (195) on a long skinny handle, drag and scrape the cells to where they want. In certain embodiments, the device includes a strong external magnet (195) that will lift the metallic bar scrapper (190') to the membrane (130) and by pulling the external magnet (195) away from the metallic bar scrapper (190'), the metallic bar scrapper (190') will fall to a desired location.

As depicted in FIG. 5A-7, in certain embodiments of the invention the system capture and incubation housing or container (100) may include a holder or pedestal (160) to position the culture base (110) as desired.

Figure 8:
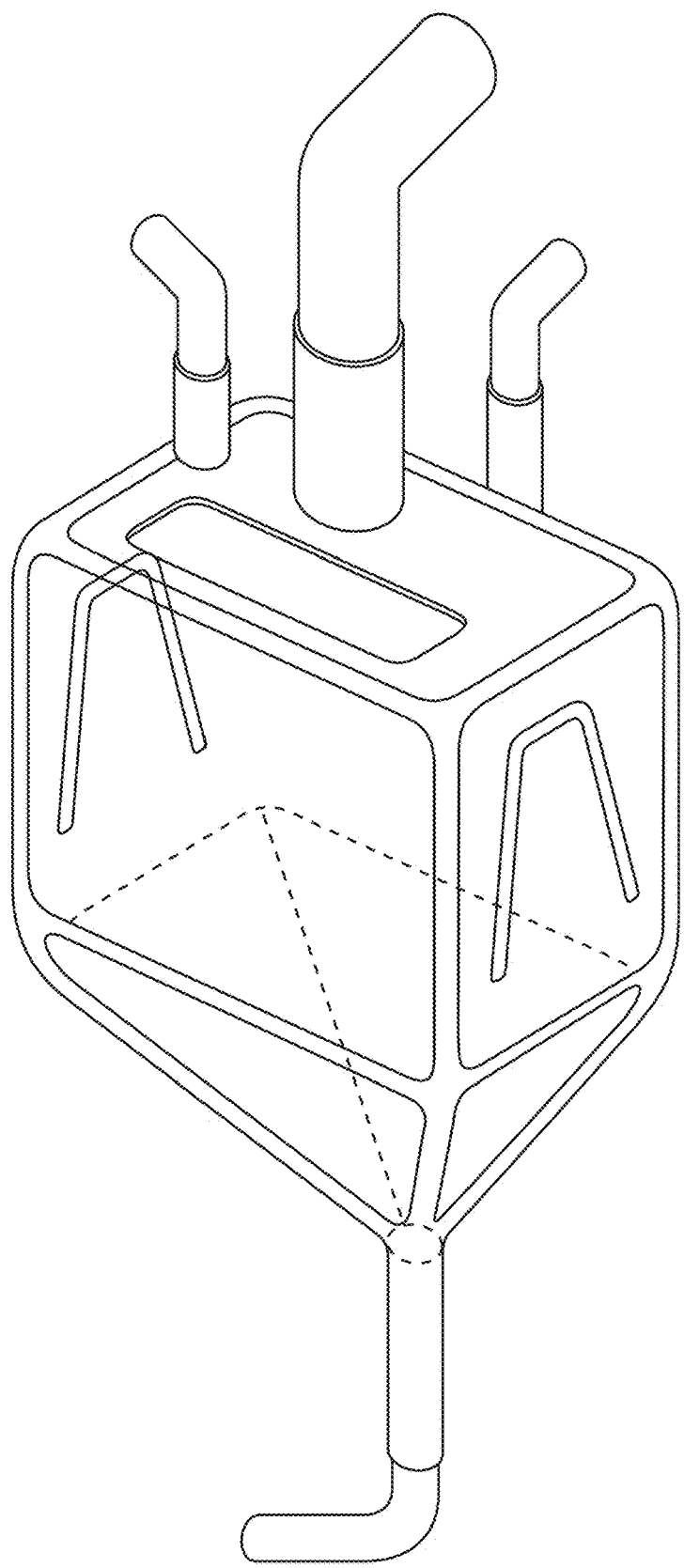
FIG. 8 is a passive ventilation closed system bioreactor of an embodiment of the present invention.

As depicted in FIG. 8, a passive ventilation closed system bioreactor of an embodiment of the invention is shown. The passive ventilation closed system bioreactor eliminates the centrifuge bucket to hold a device and acts as its own centrifuge bucket. In certain embodiments, the passive ventilation closed system bioreactor has flanges designed into two sides to fit onto the centrifuge rotor. It is specific to centrifugation on its own.

In certain embodiments, the bottom angled section of FIG. 8 includes a plurality of 2 mm beads. In certain embodiments, a mesh screen is provided within the system of FIG. 8 about 0.3 centimeters or so above the bottom port to trap the beads inside after centrifugation, but to allow dislodged blood cells to escape and be sterile collected via sterile connection.

In certain embodiments, a sterile connection device is further added to the system of FIG. 8.

In certain embodiments, the passive ventilation closed system bioreactor includes a fitted cap, preferably made of plastic, to cover the membrane when the device is removed form an incubator in use. This cap, or temporary cap, over the membrane would prevent the change of the internal environment of the bioreactor over a short removal time from the gas controlled incubator. This prevents cells in the system from being negatively affected by the change in environment.

Washing of Cells

In certain embodiments, of the invention, the method includes a process and procedure for washing cells prior to introduction of the cells into the bioreactor.

In certain embodiments, the washing of cells will be accomplished by sterile docking 600 ml transfer bags on one end of the device. The process involves adding saline to the housing to flush the system, so that the other end of the device, the waste (effluent) is captured and centrifuged along with the concentrated cells. The concentrated cells can then be reintroduced into the housing after the washing.

Cell Growing Procedure

In certain embodiments, the cell growing procedure is as follows:

1. Add apheresis cells to CD14 Ab coated container at 2×10e6 monocytes/cm2;
2. Incubate 37 degrees C. for 30-60 min;
3. Gently shake (can be mechanized) and wash off cells via sterile docking outlet with a large bore tubing;
4. Wash via 2× using sterile docking inlet and sterile docking outlet;
5. Add media and Growth Factors (GFs);
6. Incubate 3 days;
7. Re-feed via sterile docking inlet;
8. Day 6 add virus via sterile docking inlet;
9. Incubate 2 hours, wash via sterile docking inlet with 3× media exchange and sterile docking pig tail outlet with cell retainer for feeding;
10. Incubate with activation as desired or harvest via outlet for cryopreservation. One can concentration using outlet with cell retainer and peristaltic pump.

This protocol is exemplary and the additional protocols are possible using the device and methods sets forth in this application.

Device Construction

In certain embodiments, the device includes three parts, the base, the membrane, and the frame that will go around the perimeter and be sealed by any of the following means—interference fit alone; interference fit with a solvent sealing agent or glue or silicon; screws; a gasket may be employed, sonically welded, or combinations of various means.

In certain embodiments, the device further includes a gasket.

In certain embodiments, the base has a slotted interior perimeter as to allow a membrane that has been previously precut to size to fit into the slotted lip and slotted frame.

In certain embodiments, the membrane will be sealed by any one of the following means: interference fit alone; interference fit with a solvent sealing agent or glue or silicon; screws; a gasket may be employed, sonically welded, or combinations of various means.

In certain embodiments, the gas permeable membrane is located on gravitational top of the housing.

In certain embodiments, the gas permeable membrane is located on a side wall of the housing to provide for increase release of cell waste products, as $CO_2$ is a heavy gas and having the gas permeable membrane located on a side wall of the housing will increase $CO_2$ release from the housing.

In certain embodiments, the device is 1 cm tall or taller, depending upon the cells incubated in the device. In certain embodiments, the device is between 4 and 6 cm.

In certain embodiments, the device is stackable and/or flipable.

In certain embodiments, the device includes a drip or pump feeding at a very low rate for adding fresh media continuously.

In certain embodiments, the device includes a vertical separation member in the middle of the device so that various groups of cells can be cultured separately from one another.

In certain embodiments, pumped gas could be used to assist in emptying the housing and to remove cells and media.

In certain embodiments, the device includes one or more support posts to support the gas permeable membrane. In certain embodiments, the support posts are small (preferably about 1 cm in diameter) and rounded at the base and top. The gas permeable membrane is supported by the support posts.

In certain embodiments, the gas permeable membrane will overlap the top frame to the base, the base, and how the membrane will "sandwich" in with the slots. This gives exposure to solvent fixation from polystyrene to polystyrene as a preferred sealing method. The "slot and sandwich" approach goes for all the devices, regardless of shape.

In certain embodiments, the device is stackable on top of one another and configured to be inserted within a centrifuge. In certain embodiments, two or more devices are stackable on top of one another and configured to be inserted within a centrifuge. In certain embodiments, this configuration enhances cell washing and concentration.

In certain embodiments, the device is configured to lay flat, on its end and placed into a centrifuge.

In certain embodiments, the device eliminates the needs for magnetic beads within the housing that separate processing of cells.

In certain embodiments, the gas permeable membrane suspends over the top of the housing and is a lattice type framework to allow oxygen and carbon dioxide gas transpiration into and out of the housing.

In certain embodiments, the device allows for positive and/or negative selection of blood and/or blood components such as stem cells, leukocyte subsets, or other pre-determined cell or tissue lines to be introduced into the housing of the device.

These components are sterilely introduced into the housing, specifically adhered within the housing, and captured within the interior of the housing. Positive selection means the desired cell or tissue is biologically attached within the invention, conversely, negative selection occurs when unwanted cells are attached within the invention allowing wanted cells to be retrieved from the invention by the use of the pre-attached tubing.

In certain embodiments, the interior of the housing is made of polystyrene or other materials with a suitable charge, is manufactured to provide acceptable adherent properties (hydrophilic) either at the GMP manufacturing facility or at the end users site under GMP conditions (for example, by gamma irradiation) to facilitate attachment of targeted cellular receptors or affinity reagents.

In certain embodiments, the housing has or develops an adherent surface that allows this coating step within the invention. The coating will be such as a monoclonal antibody, or other, that adheres to the interior surface of the invention.

In certain embodiments, the cellular introduction and subsequent attachment of a desired cell's surface receptor to the already attached monoclonal antibody or targeted receptor within the housing, thereby causing the desired membrane ligand to bind with the monoclonal antibody/receptor within the housing (positive selection). The housing is placed in an incubator for two-hours (can be variable) that allows for an antibody/receptor interaction with the membrane ligand.

Following incubation, the unwanted cells are removed by various FDA accepted means such as buffered saline or trypsin via pre-attached PVC tubing. After removal of unwanted cells, a fourth phase occurs for further manipulation of the desired cells or tissues, this is achieved within the invention by introduction of cell culture media and cytokine growth factors. Specifically, the present invention relates to systems and methods to handle, preserve viability, separate, filter where appropriate, collect, manipulate, and/or culture ex vivo various hematological materials including red blood cells, white blood cells, tissues, and blood plasma such that, depending upon at least in part, the desired hematological CD target. Selected cells in the invention are matured, expanded in numbers, and viability retained within the invention.

In certain embodiments, the present invention may also be used for collection and manipulation of other biological materials and organisms including viruses, prions, spores, fungi, and the like. The invention is designed with legs at the four curved corners allowing for even temperature distribution to surround the invention in the incubator. The legs also allow for stacking of multiple devices within an incubator and for storage. In certain embodiments, the legs are stackable legs that extend at the bottom and the top of the device.

In certain embodiments, the device includes magnetic bars that are used for scraping the bottom of the housing to encourage cell release for cells stuck to the bottom adherent complex. This would aid in drawing a small portion of the cells to an exit port or scrape the entire bottom for total cell release. The bar would be coated with Teflon or silicon or other inert material.

In certain embodiments, the scrapper inside the device would not be a magnet, rather it would be metallic and would be controlled by an external magnet. One could position the scrapper by flipping the device over, guide the scrapper over a specific area attracted through the membrane, and then from the bottom using the magnet on a long skinny handle, drag and scrape the cells to where they want.

In certain embodiments, the device includes a strong magnet that will lift the metallic scrapper to the membrane and by pulling away from the metallic scrapper the scrapper will fall to a desired location.

In certain embodiments, the housing includes a 2 to 4-micron mesh or other filter type within the device to prevent cell loss when emptying. In certain embodiments, the mesh is positioned away from the exit ports. In certain embodiments, the mesh has a curved shape towards the inside that is positioned to capture cells.

Having thus described several embodiments for practicing the inventive method, its advantages and objectives can be easily understood. Variations from the description above may and can be made by one skilled in the art without departing from the scope of the invention.

Accordingly, this invention is not to be limited by the embodiments as described, which are given by way of example only and not by way of limitation.

The invention claimed is:

1. A sterile, passively vented closed bioreactor system for collecting and incubating living cells or other biological materials comprising:
   a housing configured to house living cells or other biological material, wherein the housing includes a sidewall and an exterior surface, wherein the housing has a conical bottom structure;
   at least one port formed in the sidewall of the housing for introduction or extraction of the living cells or other biological material through the port while maintaining interior system sterility of the system;
   a gas permeable membrane for passive ventilation of the housing; and
   a frame support configured to secure the gas permeable membrane on an exterior surface of the housing, wherein the gas permeable membrane is affixed to the frame support, wherein the gas permeable membrane fully surrounds the frame support, so as to encompass an exterior surface of the frame support, wherein the housing, the frame support, the at least one port, and the gas permeable membrane are configured to provide for multi-day to multi-month incubation and manipulation of the living cells or other biological material within an interior of the housing without the use of pumps or mechanically induced motion,
wherein the interior sterility of the system is maintained during multi-day to multi-month incubation and manipulation of the living cells or other biological material within an interior of the housing, and
wherein the housing, the frame support and the at least one port, and the gas permeable membrane are fixed to one another during the multi-day to multi-month incubation and manipulation of the living cells or other biological material within an interior of the housing to form the sterile, passively vented closed bioreactor system.

2. The system of claim 1, wherein the frame support is porous.

3. The system of claim 1, wherein the frame support is attached to the housing by at least one of the group consisting of friction or interference fit, friction or interference fit with a sealing agent, a screw, a gasket, sonic welding, laser welding, and combinations thereof, such that the attachment occurs prior to use of the system.

4. The system of claim 1, wherein the sidewall includes a lip, wherein the frame support fits within the lip to secure the frame support to the housing.

5. The system of claim 4, wherein the gas permeable membrane is configured to extend beyond the lip in the sidewall of the housing, the gas permeable membrane configured to seal the system such that all gases entering or exiting the system must pass through the gas permeable membrane.

6. The system of claim 1, wherein the housing includes a flange, the flange configured to allow a user to hold the system.

7. The system of claim 1, wherein the housing includes supports, wherein the supports are configured so that the housing is stackable on a second housing.

8. The system of claim 1, wherein the housing is rectangular, square, or circular or conical.

9. The system of claim 1, wherein the system is configured to be inserted into a centrifuge.

10. The system of claim 1, wherein the system allows for gas exchange such that carbon dioxide is exchanged into or out of the system and oxygen passes into or out of the system.

11. The system of claim 1, wherein the system is a closed system which allows for selected gases to pass in and out of the system.

12. The system of claim 1, wherein a gas pressure within the system is greater than atmospheric pressure.

13. The system of claim 1, wherein the housing further includes gas adjusted culture media located within the interior of the housing, the gas adjusted culture media configured to support the living cells or other biological material, wherein the culture media may over fill or under fill the housing within the system.

14. The system of claim 1, wherein the interior of the housing maintains sterility during system use by use of at least one sterile connection or functionally closed sterile docking port.

15. The system of claim 1, wherein an interior surface of the housing is at least partially hydrophilic, and wherein an agent introduced to the interior of the housing adheres to at least a portion of the housing interior surface.

16. The system of claim 15, wherein the agent is selected from the group including an antigen, an antibody, a major histocompatibility immune complex (WIC), a retronectin reagent, and combinations thereof.

17. The system of claim 16, wherein the agent adheres to the housing via a charge related to the internal surface of the housing.

18. The system of claim 1, wherein the interior surface of the housing includes a microstructure selected from the group including a coating solution, a gel coating solution, a retronectin reagent, a cytomatrix to allow capture of a portion of cells or biologics during centrifugation for release of a portion of cultured cells or biologics, microbeads, larger or macro polystyrene beads, and combinations thereof.

19. The system of claim 1, wherein the gas permeable membrane is selected from the group including a non-Class V1 polydimethylsiloxane, a medical grade Class V1 polydimethylsiloxane or a similar gas permeable silicon, a fluoroethylene-propylene, a natural gas permeable exchange membrane, and combinations thereof.

20. The system of claim 1, wherein the housing comprises:
an antigen adhering capability provided on a gravitational bottom surface, or bead or cytomatix of the interior of the housing for selectively collecting subsets of various types of blood cells, wherein a specific blood cell antibody identifies a specific antigen for selectively collecting subsets of various types of cells within the interior of the housing.

21. The system claim 1, wherein the gas permeable membrane is located at or near the top of the housing to facilitate cell incubation for a period of days to weeks via selective gas exchange.

22. The system of claim 1, wherein the gas permeable membrane is located at or near the top of the housing to facilitate cell incubation for a period of weeks to months via selective gas exchange.

23. The system of claim 1, wherein
a first set of specific cells are sterilely introduced into the system, and
the housing is configured to provide for the growth, expansion, and/or maturation of the first set of specific cells to be collected by centrifugation or other means of cell release to include centrifugation, shaking, or chemical release into a second set of cells that grow, expand, and/or mature, and wherein
the second set of cells that have grown, expanded, and/or matured are then taken from the system and reinfused to a patient and/or cryopreserved.

24. The system of claim 1, wherein
a first set of specific cells are sterilely introduced into the system, and
the housing is configured to provide for the growth, expansion, and/or maturation of the first set of specific cells into a second set of cells that grow, expand, and/or mature, and wherein the second set of cells that have grown, expanded, and/or matured are then taken from the system and reinfused to a donee and/or cryopreserved.

25. The system of claim 1, wherein
the system is configured to receive an ex-vivo collection of a patient's living cells, wherein the system is further configured to incubate the collected living cells within the interior of the housing, such that, upon
reintroduction of the incubated living cells back to the patient, the living cells incubated by the system are now configured by maturation or the addition of cytokines, growth factors, or other to include antibodies or antigens to stimulate, activate, support, enhance, change, down regulate, up regulate, or perform other manipulations whereby the reintroduced incubated living cells are configured to recognize and kill cancer cells, to regulate or kill autoimmune cells, and perform other manipulations in regard to an immune system to create a functioning immune system.

26. The system of claim 1, wherein the system is configured to facilitate ex-vivo manipulation of a collection of donor's cells and the introduction to and incubation of the collected cells within the interior of the housing of the system, and wherein the incubated cells are then configured, following the introduction of the incubated cells to a donee, to stimulate, activate, support, enhance, change, deregulate, up regulate, or perform other manipulations, whereby making it possible to recognize and kill cancer cells, regulate or kill autoimmune cells and perform other manipulations of an immune system to create a functioning immune system.

27. The system of claim 1, wherein the system is configured for cell introduction, selection, maturation, and expansion within the system for incubation of desired cells within the interior of the housing, and the reintroduction of the incubated cells back to a patient for the improvement and/or the enrichment of their immune system.

28. The system of claim 1, further comprising
a scraper within the housing, the scraper configured to encourage cell release for cells stuck to the bottom of the housing.

29. The system of claim 28, wherein the scraper is magnetic or metallic and controlled by an external magnet.

30. The system of claim 1, further comprising a mesh screen within the housing above the conical bottom structure.

31. The system of claim 1, further comprising at least two flanges extending from the housing, the housing configured to fit within a centrifuge rotor.

32. The system of claim 1, wherein the gas permeable membrane suspends over the top of the housing and wherein the gas permeable membrane is a lattice to allow oxygen and carbon dioxide gas transpiration into and out of the housing.

33. The system of claim 1, wherein the frame support includes slots and wherein the gas permeable membrane is sandwiched in with the slots.

* * * * *